US006884415B2

(12) United States Patent
Toba et al.

(10) Patent No.: US 6,884,415 B2
(45) Date of Patent: Apr. 26, 2005

(54) ANTIOXIDATION FOOD PRODUCT, ANTIOXIDATION PREPARATION AND ANTIOXIDATION METHOD

(75) Inventors: Masamichi Toba, Tosu (JP); Shigeto Uchiyama, Miyaki-gun (JP); Reiko Ohta, Tosu (JP); Seiichi Shimizu, Tosu (JP); Shuichi Sakamoto, Kurume (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 278 days.

(21) Appl. No.: 10/023,796

(22) Filed: Dec. 21, 2001

(65) Prior Publication Data

US 2002/0064518 A1 May 30, 2002

Related U.S. Application Data

(62) Division of application No. 09/449,418, filed on Apr. 26, 2000, now abandoned, which is a division of application No. 08/367,223, filed as application No. PCT/JP94/00753 on May 9, 1994, now Pat. No. 6,228,358.

(30) Foreign Application Priority Data

May 11, 1993 (JP) .............................. 5-109643

(51) Int. Cl.$^7$ ............................... A01N 63/00
(52) U.S. Cl. ................... 424/93.45; 424/639; 424/94.4; 424/94.1; 424/94.2; 424/729; 435/252.9; 426/61; 426/531; 426/541; 426/43; 426/49; 426/52
(58) Field of Search ............................ 424/93.45, 639, 424/94.4, 94.1, 94.2, 729; 435/252.9; 426/61, 531, 541, 63, 49, 52

(56) References Cited

U.S. PATENT DOCUMENTS

| 4,029,819 | A | | 6/1977 | Michelson |
|---|---|---|---|---|
| 4,129,644 | A | | 12/1978 | Kalapissis et al. |
| 4,230,595 | A | | 10/1980 | Yamax et al. |
| 4,442,215 | A | | 4/1984 | Vognsen et al. |
| 4,673,530 | A | * | 6/1987 | Hara ................... 252/398 |
| 4,870,002 | A | | 9/1989 | Kiel |
| 4,957,749 | A | | 9/1990 | Prieels et al. |
| 5,008,119 | A | | 4/1991 | Matsubara |
| 5,284,871 | A | | 2/1994 | Graf |
| 5,336,493 | A | | 8/1994 | Poznansky et al. |
| 5,498,412 | A | | 3/1996 | Fujie |

FOREIGN PATENT DOCUMENTS

| CH | 376078 | 2/1971 |
|---|---|---|
| EP | 0207039 | 12/1986 |
| EP | 0542398 | 5/1993 |
| GB | 1/197257 | 7/1970 |
| GB | 1197257 | 7/1970 |
| JP | 51-115968 | 10/1976 |
| JP | 55007013 | 1/1980 |
| JP | 62201570 | 7/1987 |
| JP | 1243971 | 9/1989 |
| JP | 2-3495 | 1/1990 |
| JP | 2003495 | 1/1990 |
| JP | 4-41436 | 2/1992 |
| JP | 5084065 | 4/1993 |

OTHER PUBLICATIONS

ATCC Catalogue of Bacteria, pp. 169, 172 and 174–175 (1992).
Hammes et al, *In the Prokaryotes*, Springer–Verlag, II:1562 (1992).
Vanos et al, *Food Microbiol.* (LOND), 4(1):19–34 (1987).
Kono et al, *J. Act. Oxyg. Free Rad.*, 2(1):18–26 (1991).
Kono et al, *PNE–Protein Nucleic Acid and Enzy.*, 33(16):2940–2948 (1988).
Archibald, *Crit. Rev. Microbiol.*, 13(1):63–109 (1986).
Waldo et al, *J. Am. Chem. Soc.*, 114(14):5869–5870 (1992).
Kono et al, *Proced. Int. Conf.*,4:231–233 (1985).
Wheeler et al, *J. of Gen. Microbiol.*, 121(12):457–464 (1980).
Database WPI, Week 7648, corresponding to JPA 51–115698 (Hagiwara), Oct. 14, 1976.
Database WPI, Week 8945, corresponding to JPA 01–243971 (Kagome), Sep. 28, 1989.
Database WPI, Week 9213, corresponding to JPA 04–041436 (Sodex), Feb. 12, 1992.
Database WPI, Week 9318, corresponding to JPA 05–084065 (Asahi Breweries), Apr. 6, 1993.
Database WPI, Week 9007, corresponding to JPA 02–003495 (Okuno Pharm.), Jan. 9, 1990.
Patent Abstracts of Japan, Hiroyoshi, 16(213):C–0942 (1992); corresponding to JPA 40–041436 (Feb. 12, 1992).
Database WPI, Week 7351, corresponding to SUA–276078 (Moscow GV Plekhanov).
Patent Abstracts of Japan, Nippon, 12(56):C–477 (1988); corresponding to JPA 62–201570 (Sep. 5, 1987).
Patent Abstracts of Japan, Kibum, 4(30):C–002; corresponding to JPA 55–007013 (Jan. 18, 1980).
Kono et al., *J. of Bacteriology*, 155(2):742–746 (1983).
Steele et al, *Cer. J. Microbiol.*, 32:409–413 (1986).
Privake et al, *J. of Biol. Chem.*, 265(35):21966–21970 (1990).

\* cited by examiner

*Primary Examiner*—Irene Marx
(74) *Attorney, Agent, or Firm*—Sughrue Mion, PLLC

(57) ABSTRACT

The antioxidation food product of the present invention is produced by fermenting a food product containing bacteria having catalase activity, such as *Lactobacillus plantarum*, in the presence of a manganese-containing natural material. The antioxidation food product has antioxidation activity in viva, including the digestive tract, by simultaneously expressing a superoxide dismutase-like activity and a catalase activity, and is effective for preventing disease caused by active oxygen.

3 Claims, 10 Drawing Sheets

F I G. 9
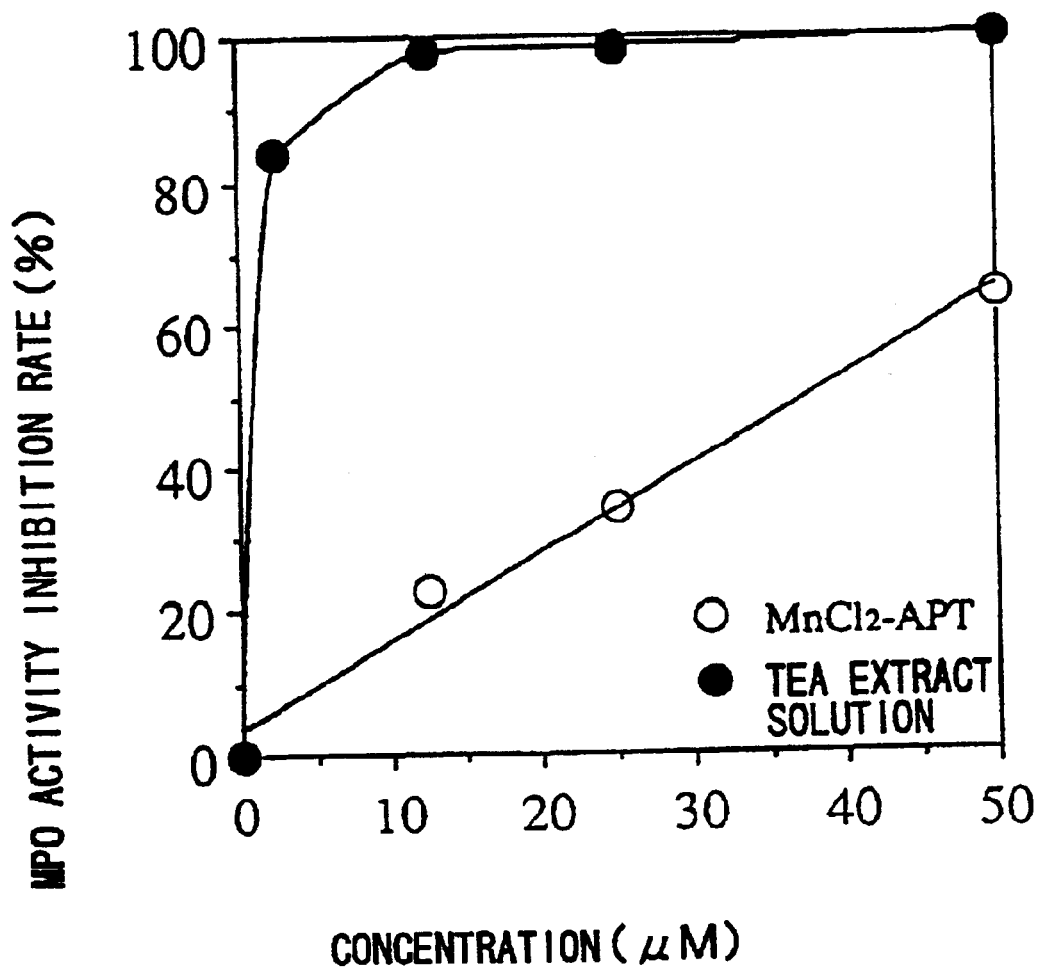

ANTIOXIDATION FOOD PRODUCT, ANTIOXIDATION PREPARATION AND ANTIOXIDATION METHOD

This application is a Divisional of U.S. Appln. Ser. No. 09/559,418, filed Apr. 26, 2000 (now abandoned); which in turn is a Divisional of U.S. Appln. Ser. No. 08/367,223, filed Jan. 10, 1995 (now U.S. Pat. No. 6,228,358); which in turn is a § 371 of PCT/JP94/00753, filed May 9, 1994. The disclosure of each of which is incorporated herein, in their entirety, by reference.

TECHNICAL FIELD

The present invention relates to an antioxidation food product, an antioxidation preparation and an antioxidation method, which aim at preventing or improving diseases caused by active oxygen, by removing superoxide ($O_2^-$) and hydrogen peroxide ($H_2O_2$).

BACKGROUND ART

Various studies on lactic acid bacteria or physiological effects of food products using lactic acid bacteria have been made since Metschnikoff's longevity theory.

As a function of lactic acid bacteria contained in fermented milk such as yogurt, for example, intestinal microflora improving effect, intestinal controlling action, etc. are well known. Recently, it has been reported that lactic acid bacteria have various functions such as immune activation action, antimicrobial action, antitumor action and the like. As described above, since various health effects are expected for lactic acid bacteria, fermented milk and lactic acid bacteria beverage using strains such as *Lactobacillus acidophilus, Lactobacillus casei* and genus Bifidobacterium, which are also detected in the human bowel, are put on the market.

By the way, active oxygen is important as a biological protection factor such as bactericidal action of leucocytes, but it becomes apparent that the excessive production of active oxygen in the living body causes various tissue disorders.

As the ordinary factors for generating active oxygen, there have been known stresses, alcohols, peroxides, drugs, exercises and the like. It is pointed out that active oxygen and lipoperoxide generated by these factors are closely connected with cerebral nerve diseases, circulatory diseases, cancers, alimentary diseases, hepatic diseases, arterial sclerosis, renal diseases, diabetes, aging and the like.

The living body retains a series of oxidation protection systems so to protect itself against oxygen toxicity. On the other hand, in order to permit these systems to function normally, it is important to ingest oxidation nutrient components sufficiently. As the natural oxidation nutrient components, there have been known vitamin E, vitamin C, s-carotene, polyphenol and trace elements (e.g. selenium, copper, zinc, etc.). For the purpose of affording an antioxidation action, food products containing these nutrient components have been developed.

In vivo antioxidation mechanism is classified roughly into a preventive antioxidation action (controlling the generation of a radical) and a linkage-breakage type antioxidation action (scavenging and eliminating a radical which has already been generated) according to its action. Examples of those which have the former action include enzymes such as superoxide dismutase (SOD), catalase (CAT), glutathione peroxidase (GSH-Px) and the like. Examples of those which have the latter action include the above antioxidation nutrient components.

However, in a conventional food product, there have never been known products which aim at conducting linkage-elimination of superoxide ($O_2^-$) and hydrogen peroxide ($H_2O_2$) which is connected with the lipid peroxidation.

It is an object of the present invention to provide an antioxidation food product, an antioxidation preparation and an antioxidation method for the linkage-elimination of superoxide and hydrogen peroxide, which express a superoxide dismutase (hereinafter referred to as "SOD")-like activity and a catalase (hereinafter referred to as "CAT") activity, simultaneously, and which are particularly superior in preventive antioxidation action.

The antioxidation food product of the present invention has an antioxidation action in the living body, comprising a fermented product produced by adding a manganese-containing natural material and fermenting with bacteria having a CAT activity. By "living body" is meant the physical body of living, multicellular organisms including, but not limited to humans and other mammals.

That is, the present inventors have obtained a knowledge that specific bacteria among various lactic acid bacteria express no CAT activity under the environment in which manganese is not present, but if manganese is present in the growing environment, they incorporate manganese into their cells to express a Mn-CAT activity and a SOD-like activity, simultaneously. The antioxidation food product of the present invention is particularly suitable as a preventive antioxidation food product.

It is known that Mn-CAT is not affected by various inhibitors, modifiers, chelating agents, etc. in comparison with heme-CAT containing iron, and exhibits stability within a wide range of pH and temperature.

Further, the antioxidation food product of the present invention may be a dried product, preferably a freeze-dried product which contains bacteria having a CAT activity and a manganese-containing natural material, in addition to the fermented product as described above by "manganese-containing natural material" is meant any material whether naturally occuring or synthetically produced which contains the element manganese bound to another organic or inorganic chemical moiety. The term is not meant to include elemental manganese.

The present invention also provides an antioxidation preparation comprising bacteria having a CAT activity and a manganese-containing natural material. This antioxidation preparation may be a dried product (in the form of tablet, powder, granule, capsule, etc.) or in the form of liquid.

Furthermore, according to the present invention, there is provided an antioxidation method in the living body including the interior of a digestive tract, which comprises ingesting a fermented product produced by adding a manganese-containing natural material to a food product and fermenting with bacteria having a CAT activity to express a SOD-like activity and a CAT activity, simultaneously.

BRIEF EXPLANATION OF THE INVENTION

FIG. 9 is a graph illustrating a MPO activity inhibition effect of a tea extract solution and $MnCl_2$.

BEST MODE FOR CARRYING OUT THE INVENTION

Figure 1:
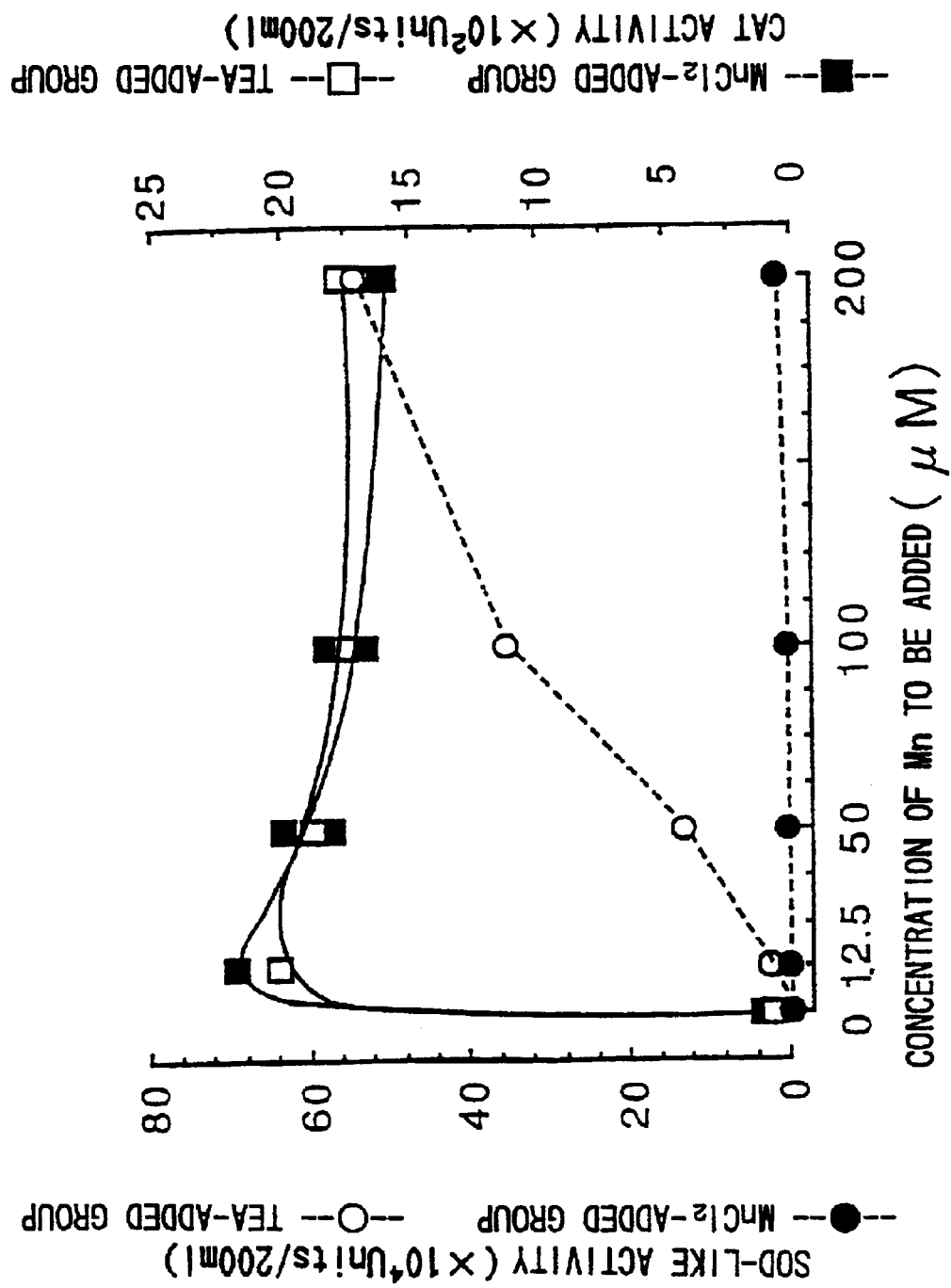
FIG. 1 is a graph illustrating a change in SOD-like activity and CAT activity due to the addition of $MnCl_2$ or tea.

Examples of the bacteria having a Mn-CAT activity in the present invention include *Lactobacillus plantarum* [ATCC14431 strain] as Lactobacillus.

In systematics of bacteria, it is said that lactic acid bacteria have no CAT activity. However, when manganese is present in the growing environment, the above-described *Lactobacillus plantarum* incorporate manganese into their cells to express a Mn-CAT activity. On the other hand, it is known that Mn acts as a center metal of SOD and Mn itself has a SOD-like activity. Accordingly, it becomes possible to produce a fermented product having a SOD-like activity and a CAT activity, simultaneously, by fermenting with *Lactobacillus plantarum* in the presence of the manganese-containing natural material.

Recently, the clinical application of SOD against 5 rheumatism, cardiac ischemia, etc. have been proceeded. However, there is a serious problem that the local amount of hydrogen peroxide is increased when SOD is used alone and, further, a hydroxy radical (○OH) having a highest radical reactivity is formed. Accordingly, it is important to eliminate $O_2^-$ and remove hydrogen peroxide by using CAT and GSH-Px in combination when employing SOD. Therefore, for the above reason, the coupling action between SOD-like and CAT obtained by adding Mn to *Lactobacillius plantarum* is considered to be very important.

Further, it is considered that the same effect as that of *Lactobacillus plantarum* can be obtained by using bacteria having a CAT activity in addition to *Lactobacillus plantarum* because manganese itself has a SOD-like activity even if no SOD is produced. Examples of the bacteria having a Mn-CAT activity other than *Lactobacillus plantarum* include *Pediococcus pentosaceus, P. acidilactici, Thermolephilum album* and the like.

Further, the antioxidation food product or antioxidation preparation of the present invention may be a dried product, preferably freeze-dried product comprising a bacteria having a CAT activity and a manganese-containing natural material, in addition to the above fermented product. The dried product can be used in any form such as powder, granule, tablet and the like. The dried product may be ingested as it is or ingested after the dried product is added to commercially available milk and the mixture is fermented to prepare yogurt. It may be also in the form of frozen product, in addition to the dried product.

The manganese-containing natural material in the present invention is used for supplying manganese to the bacteria cells. It is impossible to add manganese as an inorganic compound because manganese itself is not accepted as a food additive and, therefore, the natural material was used. Examples of the natural material containing a large amount of manganese include plants such as teas, vegetables (e.g. represented by cabbage, spinach, etc.), herbs and the like. Accordingly, it is important to add these plants so as to supply manganese which is necessary for expressing a CAT activity and a SOD-like activity to bacteria having a CAT activity. Particularly, since the tea contains a lot of antioxidation components such as catechin, vitamin C, various trace elements, etc., additional effects can be obtained by taking advantage of the presence of an activity of these anti-oxidant components.

Particularly, the addition of the tea to *Lactobacillus plantarum* causes the following effect, that is, not only the SOD-like activity and CAT activity are expressed but also the SOD-like activity is extremely high in comparison with the case using an inorganic Mn compound (e.g. manganese chloride $MnCl_2$, etc.) and, further, the SOD-like activity and CAT activity under gastric juice exposure can be maintained for a long period of time.

It is preferred that the tea or the other natural material is added to a food product in the form of powder. The incorporation of manganese due to bacteria is facilitated if the manganese source is a powder. The pulverization is conducted by extracting a natural material with water and/or water-miscible organic solvent (e.g. alcohols such as ethyl alcohol, etc.) and then with an organic solvent which is in-miscible to water (e.g. chloroform, ethyl acetate, butanol, etc.) to separate into an organic phase and an aqueous phase, recovering a dissolved solid content from the aqueous phase, followed by drying. Further, a solid content may also be recovered from a solution extracted with water and/or water-miscible organic solvent and then pulverized. Furthermore, an aqueous solution prepared by extracting the natural material with water may be added without pulverizing, or the pulverized product of the natural material may be added as it is.

Examples of the tea include green tea (non-fermented tea) such as refined green tea, powdered tea, green tea of mild grade, coarse tea, dust tea, germ tea, toasted tea, etc.; fermented tea such as black tea, etc.; semi-fermented tea such as oolong tea, paochong tea (jasmine tea), etc.

In case of the fermented product, the amount of the manganese-containing natural material (amount of manganese) is preferably about 4 to 20 mg, more preferably about 4 to 8 mg, based on 1 kg of the product. In case of the dried product which mainly comprises a bacteria cell, a manganese-containing natural material and an excipient, the amount of the manganese-containing natural material (amount of manganese) is preferably about 4 to 20 mg, more preferably about 4 to 8 mg, based on 10 g of the product.

Typical examples of the form of the antioxidation food product of the present invention include fermented food products and (freeze) dried food products, as described above.

The fermented product in the present invention includes fermented milk such as yogurt and lactic acid bacteria beverage. The fermented milk can be obtained by adding a predetermined amount of a manganese-containing natural material into 1 liter of milk or skim milk, inoculating with lactic acid bacteria having a CAT activity and fermenting at 35 to 37° C. for about 12 to 72 hours. By adjusting the amount of the lactic acid bacteria starter and manganese-containing natural material to be added, fermentation time, etc., there can be produced yogurt in the form of solid (stationary yogurt), (semi)solid (stirred yogurt) and liquid (drink yogurt). Further, sweeteners (e.g. glucose, sucrose, etc.), flesh (e.g. grapefruit, apple, orange, lemon, etc.), inorganic electrolytes as a mineral source (e.g. sodium chloride, potassium chloride, magnesium chloride, calcium chloride, etc.), vitamins, flavors, etc. may be added appropriately to the fermented milk.

Further, a lactic acid bacteria beverage can be obtained by adding a predetermined amount of a manganese-containing natural material to a mixed solution of skim milk and sugar (e.g. glucose, sucrose, etc.), inoculating the mixed solution with lactic acid bacteria having a CAT activity and fermenting at 35 to 37° C. for about 12 to 72 hours. Yogurt (e.g. liquid yogurt type, juice type, etc.) can be produced according to a proportion of skim milk to a diluting solution (e.g. water, fruit juice, etc.). As the base to be fermented, for example, there can be used milk serum, low fat milk, etc., in addition to skim milk. Examples of the diluting solution include flesh, lactocoffee, etc., in addition to water.

The dried product in the present invention is obtained by mixing about $5 \times 10^8$ to $5 \times 10^{10}$ bacteria cells 20 with 2 to 4 g of a manganese-containing natural material, adding an excipient to the mixture, followed by drying. Examples of the excipient include lactose, glucose, sucrose, oligosaccharide and the like.

The dried product in the present invention may be ingested as it is or ingested after the dried product is added to milk and the mixture is fermented at room temperature for 12 to 24 hours to prepare yogurt in the ordinary home.

FIELD OF INDUSTRIAL APPLICABILITY

As described above, the antioxidation food product and antioxidation preparation of the present invention can express a SOD activity and a CAT activity, simultaneously, and remove superoxide and hydrogen peroxide. Therefore, they are effective for preventing diseases caused by active oxygen.

EXAMPLES

Test Example 1

(in vitro SOD-like activity and CAT activity of tea-added product produced by fermenting with *Lactobacillus plantarum*)

When *Lactobacillus plantarum* is cultured (fermented) in an APT broth (containing "bacto tryptone" commercially available from DIFCO Ltd., yeast extract, glucose, sodium citrate, sodium chloride, dipotassium hydrogen phosphate, magnesium sulfate and sodium carbonate), $MnCl_2$ or tea (powdered green tea) were added in the medium so that the concentration of Mn may be 12.5 µM, 50 µM, 100 µM and 200 µM, respectively, and the SOD activity and CAT activity of bacteria cells and the whole medium containing $MnCl_2$ or tea after culturing for 16 hours at the point where the multiplication of bacteria reaches the maximum were examined.

The SOD-like activity was determined by a NBT reduction method and the CAT activity was determined by a decrease rate of hydrogen peroxide. The results are shown FIG. 1.

As shown in FIG. 1, the SOD-like activity increased in proportion to the amount of Mn to be added in both cases (addition of $MnCl_2$/tea), but the absolute value of the SOD-like activity is about 35 times greater when tea is added than when 200 M of the Mn is added.

The CAT activity was lower than the limit of detection when Mn is not added. On the other hand, by adding 12.5 µM or more of Mn, an activity of about 1800 U/200 ml of APT medium was expressed in both cases that (addition of $MnCl_2$/tea).

The function of SOD and CAT is the elimination of $O_2^-$ and $H_2O_2$. However, SOD and CAT are enzymes and, therefore, it is said that SOD and CAT are devitalized even if they are orally ingested and no effect is obtained. However, since the SOD activity and CAT activity are retained in the bacteria cells in case of the Mn-added product produced by fermenting with *Lactobacillus plantarum*, it is expected that these activities are retained until the bacteria are killed. Further, as described above, since Mn itself and the component in the tea have a SOD-like activity but they are not enzymes, it is considered that they are not easily devitalized.

In order to prove the above description, the tea-added product produced by fermenting with *Lactobacillus plantarum* was orally administered to a pylorus-ligated rat, forcibly, and a change in SOD-like activity and CAT activity with time after administration was examined in the following Test Examples.

Test Example 2

(Retention of SOD-like activity and CAT activity of a product produced by fermenting with *Lactobacillus plantarum* in stomach of pylorus-ligated rat)

Figure 2:
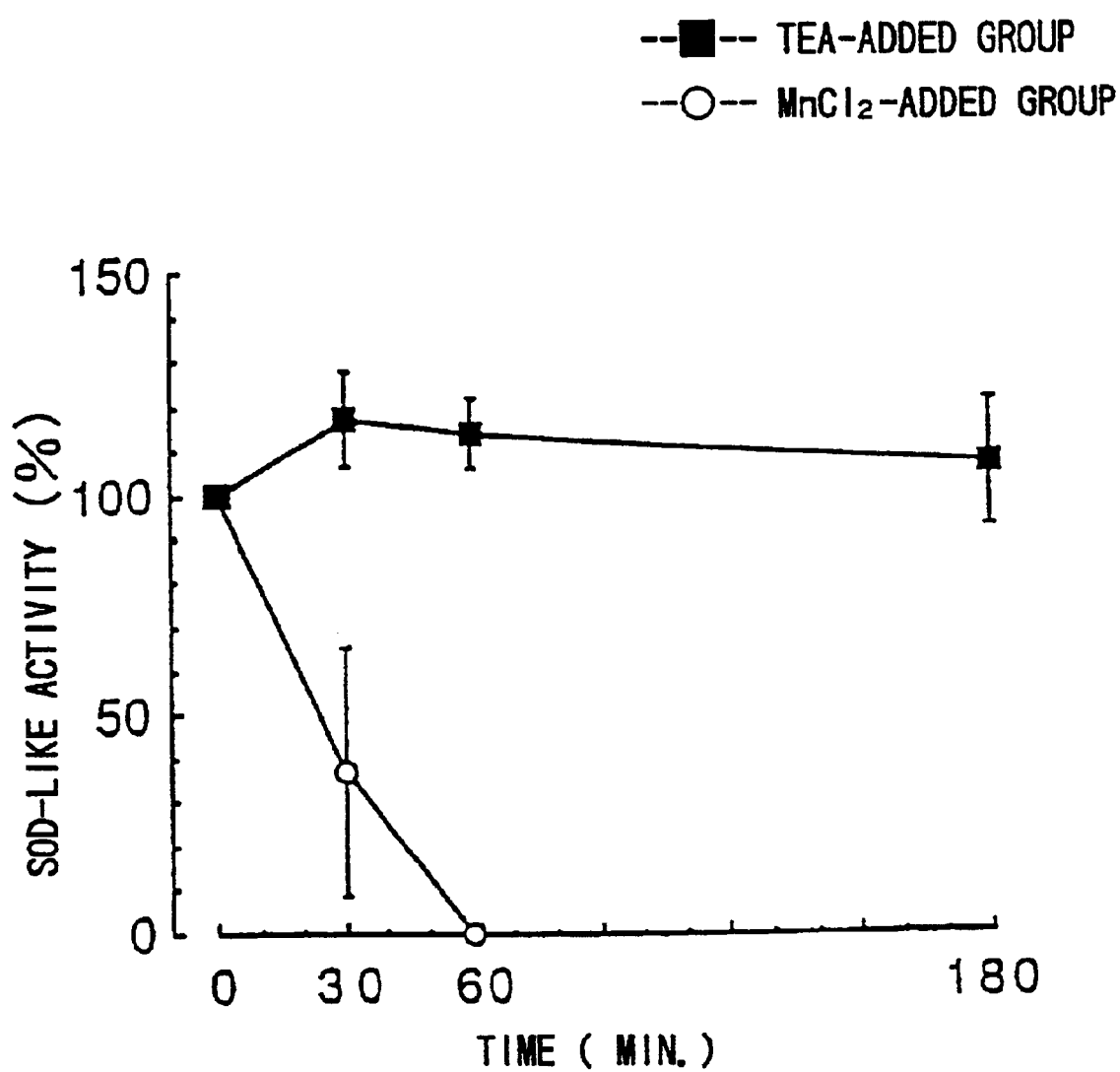
FIG. 2 is a graph illustrating a change in SOD-like activity with time after the administration of a product produced by fermenting with *Lactobacillus plantarum* in a pylorus-ligated rat.
Figure 3:
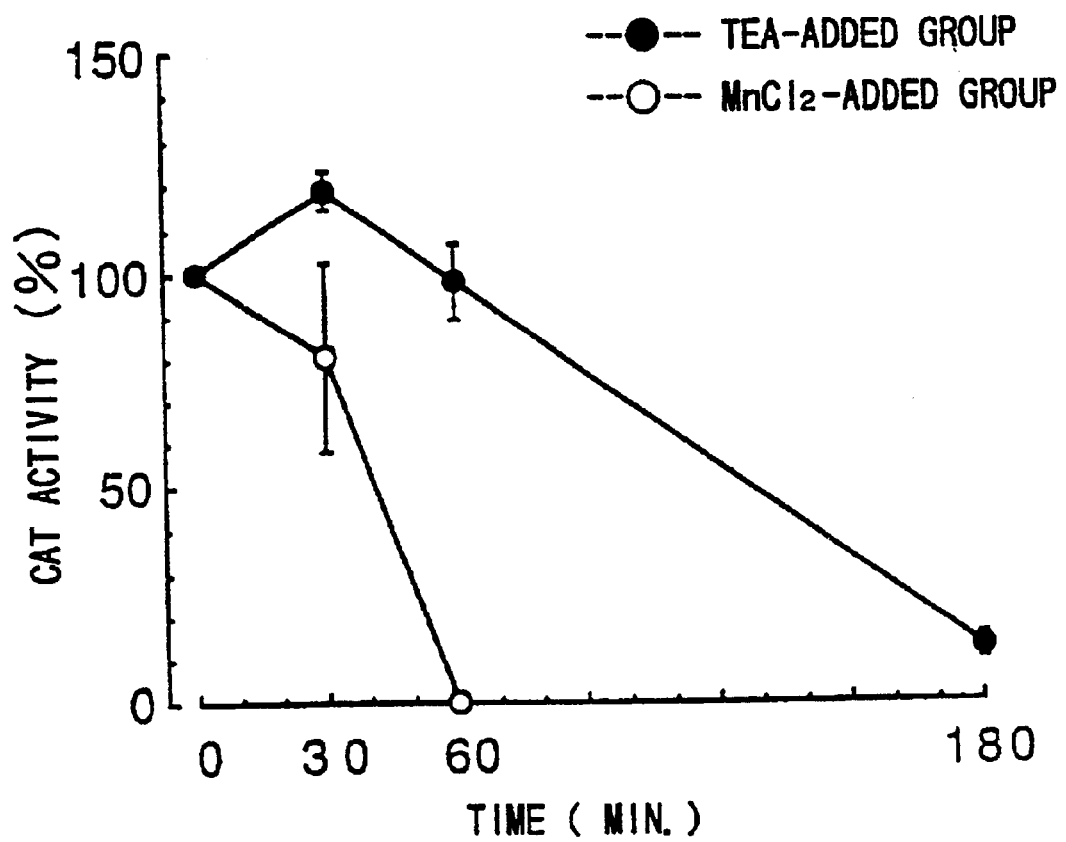
FIG. 3 is a graph illustrating a change in CAT activity with time after the administration of a product produced by fermenting with *Lactobacillus plantarum* in a pylorus-ligated rat.

Immediately after ligating the pylorus of SD male rats (weight: 250 g), 5 ml of a product produced by fermenting with *Lactobacillus plantarum* was administered using an oral probe and contents in the stomach were recovered with time to examine a change in SOD-like activity and CAT activity. The results are shown in FIGS. 2 and 3. Further, a test product was obtained by adding $MnCl_2$ or a tea (powdered green tea) in the concentration (concentration of Mn) of 50 µM to an APT broth and, after inoculating with *Lactobacillus plantarum*, fermenting for 16 hours.

As shown in FIG. 2, in case of the addition of $MnCl_2$, the SOD-like activity decreased to about 35% of the initial value for 30 minutes and was eliminated until 60 minutes have passed. On the contrary, in case of the addition of tea, high activity was retained until 3 hours have passed.

As shown in FIG. 3, in case of the addition of $MnCl_2$, the CAT activity decreased to about 80% of the initial value for 30 minutes, similar to the SOD-like activity. On the other hand, in the tea-added group, the CAT activity increased by about 20% of the initial value and the same activity as that of the initial value was expressed for 60 minutes. Further, little (about 15%) activity was retained after 3 hours.

Figure 4:
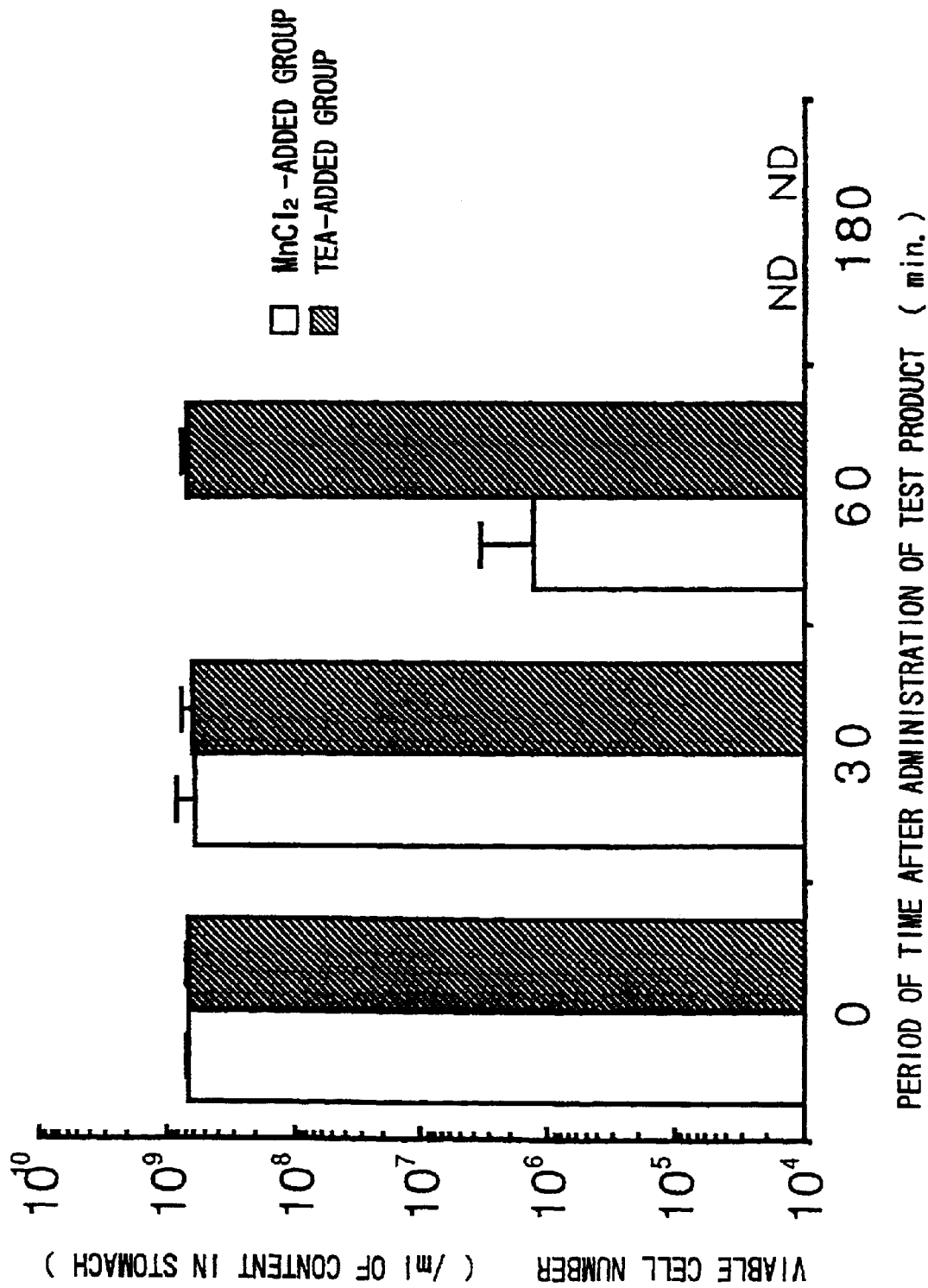
FIG. 4 is a graph illustrating a change in viable cell number in the pylorus-ligated stomach.

As shown in FIG. 4, the viable cell number after oral administration decreased to about 1/1000 of the initial value for 60 minutes, in case of the addition of $MnCl_2$. After 3 hours, bacteria cells were not detected. On the other hand, in the tea-added group, the viable cell number before administration was retained until 60 minutes have passed. After 3 hours, bacteria cells were not detected. In FIG. 4, "ND" means that the viable cell number is lower than the limit of detection ($10^4$).

As described above, it became apparent that, by adding a tea to *Lactobacillus plantarum*, not only the SOD-like activity and CAT activity are expressed, but also high activity is retained for a long period of time in comparison with Mn contained in the inorganic compound such as $MnCl_2$. It is considered that this is caused by the retention of the viable cell number in the stomach.

Test Example 3

(SOD-like activity of water-soluble fraction of tea before and after lactic fermentation)

Figure 5:
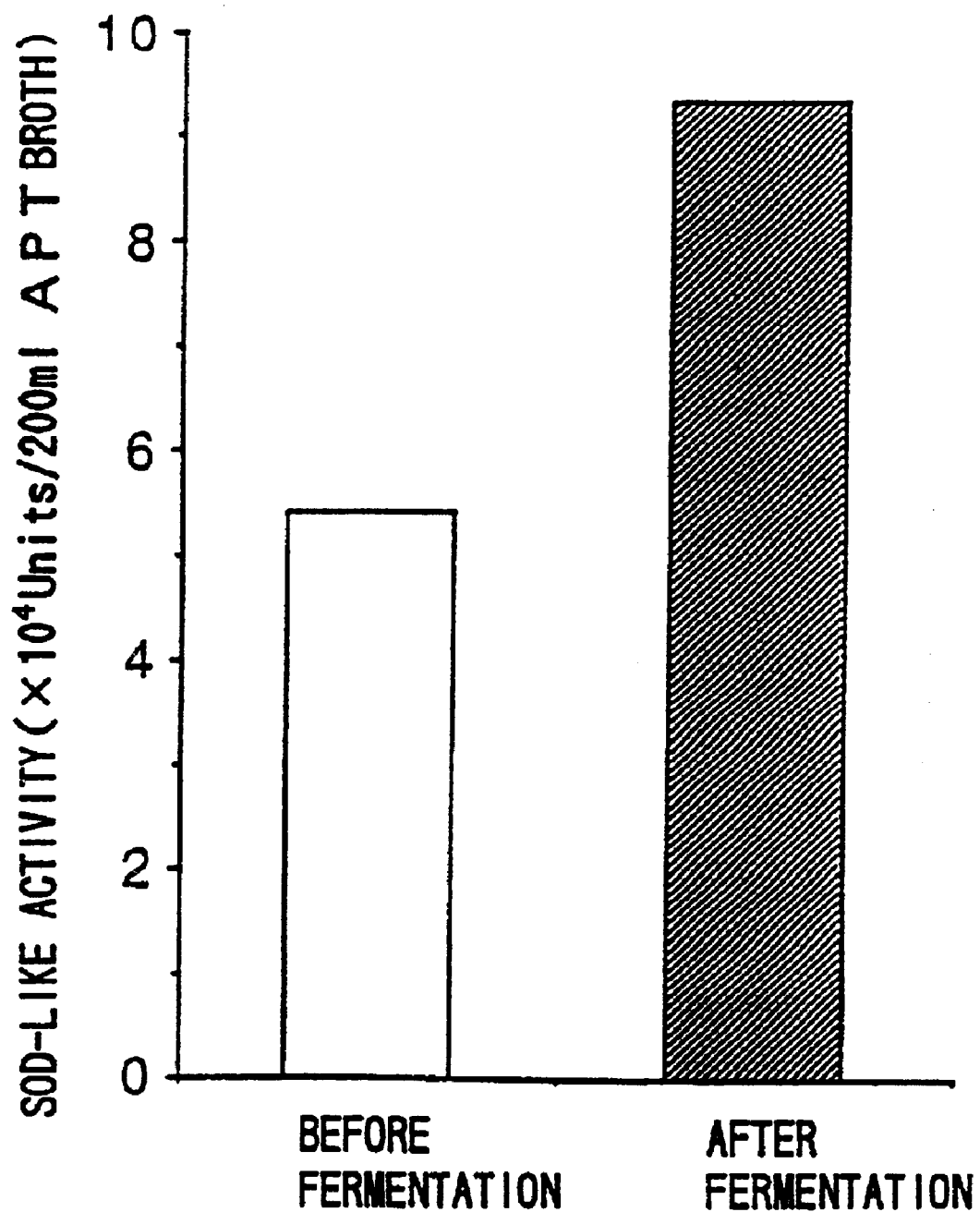
FIG. 5 is a graph illustrating a SOD-like activity before or after the fermentation of a tea-added product produced by fermenting with *Lactobacillus plantarum*.

As described above, high SOD-like activity can be obtained when the tea is added. Actually, a tea (powdered green tea) was added to a APT broth in the concentration (concentration of Mn) of 50 $\mu$M and the medium was allowed to stand at normal temperature for 24 hours to give a water-soluble fraction (supernatant on the medium before fermentation). Then, the SOD-like activity of the water-soluble fraction was measured. As a result, as shown in FIG. 5, the SOD-like activity before fermentation was high, 54,040 U/200 ml of APT broth.

On the other hand, the SOD-like activity of a water-soluble fraction obtained by inoculating the above-described tea-added APT broth wherein Mn has been added in the concentration (concentration of Mn) of 50 $\mu$M with *Lactobacillus plantarum* and fermenting for 16 hours was measured. As a result, as shown in FIG. 5, the SOD-like activity after fermentation was about 93,400 U/200 ml of APT broth.

As is apparent from these results, it was observed that the activity increased by about 1.7 times that before fermentation by the fermentation. The reason is considered to be as follows. That is, the antioxidation component could be present in more effective form by utilizing the tea into *Lactobacillus plantarum*. From this point of view, the effect for adding the tea to *Lactobacillus plantarum* can be confirmed.

Test Example 4

(Suppression of gastric mucosal lesions due to oral administration of product produced by fermenting with *Lactobacillus plantarum*)

(1) Effect in indomethacin gastric ulcer model

20 Mg/kg of indomethacin was subcutaneously administered to SD male rats (weight: 250 g) and the effect of the product produced by fermenting with *Lactobacillus plantarum* to the formation of gastric ulcer after 6 hours was examined. As the product produced by fermenting with *Lactobacillus plantarum*, those which obtained by adding a tea extract solution (those obtained by extracting 100 g of a green tea with 1 liter of hot water) to an APT broth in the concentration (concentration of Mn) of 50 $\mu$M and, after inoculating with *Lactobacillus plantarum*, fermenting for 16 hours.

The test product was as follows.

(a) Group of tea-added product produced by fermenting with *Lactobacillus plantarum*: It is obtained by preparing a tea extract solution so that its SOD-like activity may become 24,000 units/ml and adding the extract solution to a product produced by fermenting with *Lactobacillus plantarum*. The viable cell number of *Lactobacillus plantarum* was $6.3 \times 10^9$ cells/ml.

(c) Control group: only APT broth

The test product was orally administered 2 times with a dose of 2.5 ml every 3 hours after indomethacin was subcutaneously administered.

Figure 6:
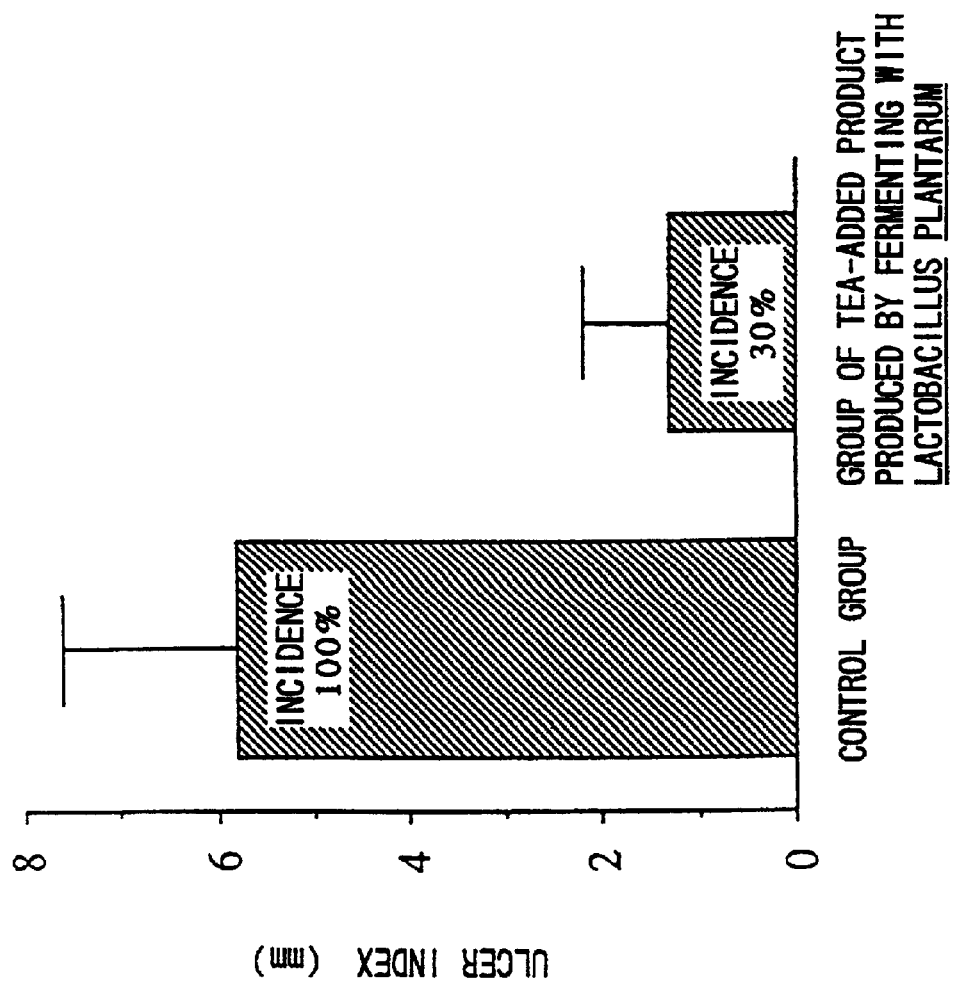
FIG. 6 is a graph illustrating an effect after the administration of a tea-added product produced by fermenting with *Lactobacillus plantarum* in an indomethacin-induced gastric ulcer model.

The results are shown in FIG. 6. FIG. 6 is a graph illustrating an ulcer index of each group after 6 hours have passed since subcutaneously administration of indomethacin with the average value±standard error of 10 rats. As shown in FIG. 6, the ulcer index of the control group was 5.8±1.8 mm. Further, it was confirmed that ulcer was generated in all 10 rats in the control group. To the contrary, in the group of the product produced by fermenting with *Lactobacillus plantarum*, the suppression was conducted significantly in comparison with the control group (p<0.05)

Figure 7:
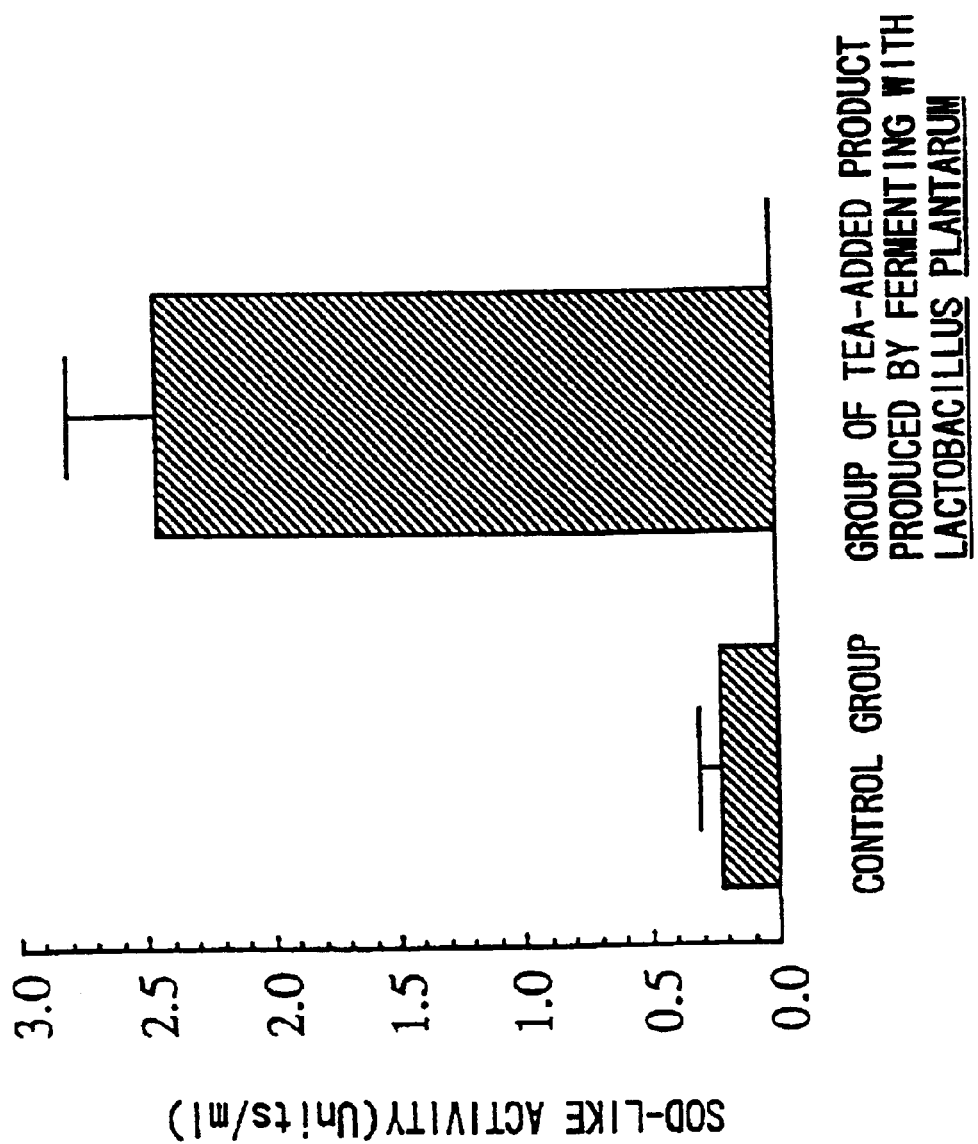
FIG. 7 is a graph illustrating a SOD(-like) activity in serum after the administration of a tea-added product produced by fermenting with *Lactobacillus plantarum*.

The evaluation due to the ulcer index and the measurement of the SOD-like activity which is present in a serum deproteinized component after the administration of the test product were conducted, simultaneously. As a result, as shown in FIG. 7, the SOD-like activity in the deproteinized component was 0.23±0.08 units/ml in the control group. To the contrary, the group of the tea-added product produced by fermenting with *Lactobacillus plantarum*, a significant increase, 2.34±0.33 units/ml (p<0.01) was exhibited.

(2) Effect in hydrogen peroxide-induced gastric mucosal lesions model

In order to prepare gastric mucosal lesions due to hydrogen peroxide, SD male rats (weight: 250 g) were subjected to a pylorus-ligation operation and diethylmaleic acid (0.75 ml/kg) was subcutaneously administered as a depletion agent of glutathione in the tissue. Then, 0.5 ml of 7.5% hydrogen peroxide was orally administered and the effect of the product produced by fermenting with *Lactobacillus plantarum* to the gastric mucosal lesions after 3 hours was examined.

As the product produced by fermenting with *Lactobacillus plantarum*, were obtained by adding $MnCl_2$ or a tea extract solution (those obtained by extracting 100 g of a green tea with 1 liter of hot water) to an APT broth in the concentration (concentration of Mn) of 50 $\mu$M and, after inoculating with *Lactobacillus plantarum*, fermenting for 16 hours.

The test product was as follows.

(a) Group of product produced by fermenting with *Lactobacillus plantarum*: It is obtained by fermenting with $MnCl_2$.

(b) Group of tea-added product produced by fermenting with *Lactobacillus plantarum*: It is obtained by preparing a tea extract solution so that its SOD-like activity may become 24,000 units/ml and adding the extract solution to a product produced by fermenting with *Lactobacillus plantarum*. The viable cell number of *Lactobacillus plantarum* was $6.3 \times 10^9$ cells/ml.

(c) Tea group: It is obtained by preparing a tea extract solution so that its SOD-like activity may become 2,400 units/ml and adding the extract solution to an APT broth.

(d) Control group: only APT broth

The test product was orally administered with a dose of 2.5 ml immediately before the administration of hydrogen peroxide.

Figure 8:
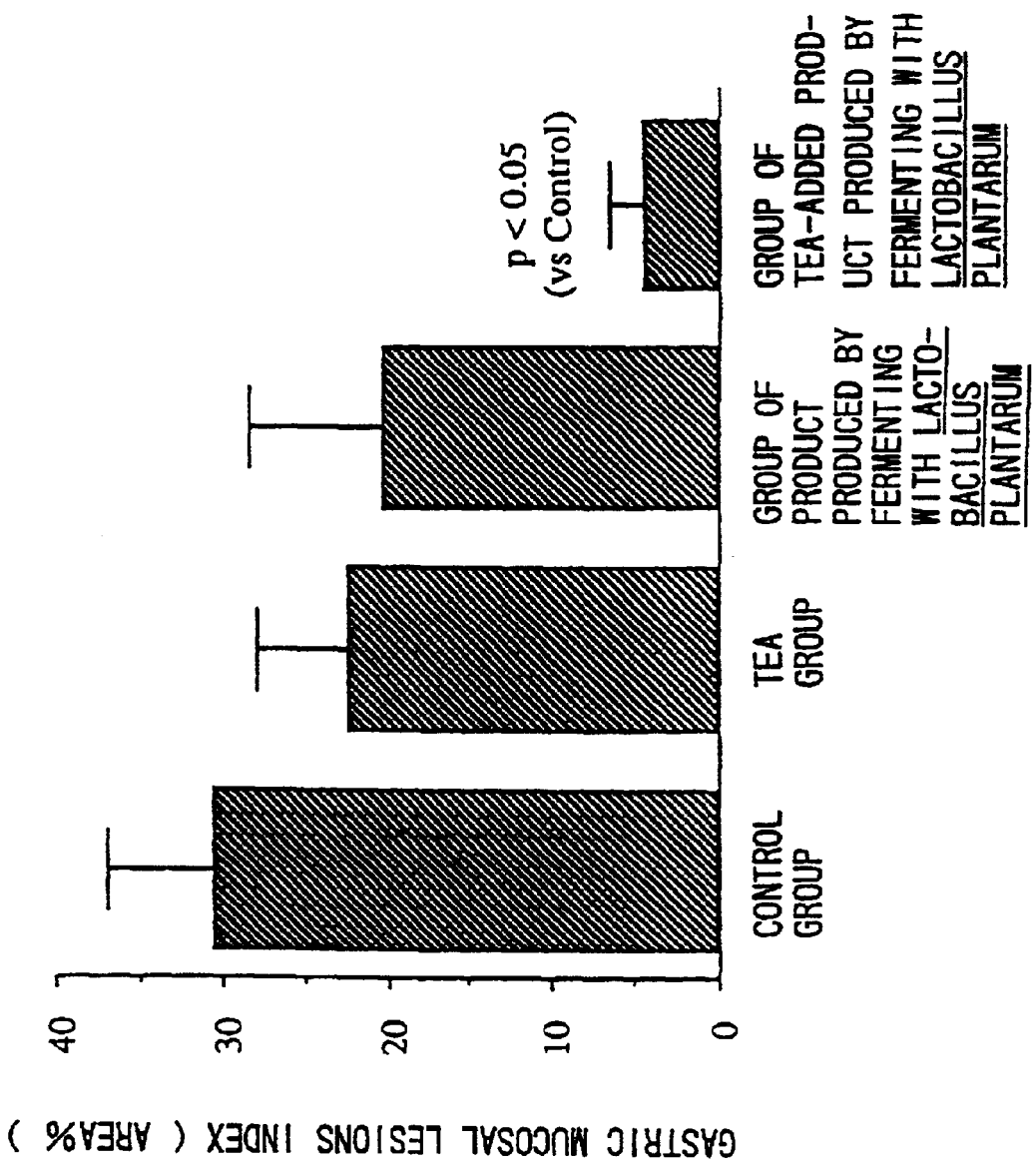
FIG. 8 is a graph illustrating an effect after the administration of a tea-added product produced by fermenting with *Lactobacillus plantarum* on hydrogen peroxide-induced gastric mucosal lesions.

The results are shown in FIG. 8. FIG. 8 is a graph illustrating an average value and a standard error of a gastric mucosal lesions index (area %) of 10 rats. As shown in FIG. 8, the erosions area was 30.60±6.34% in the control group. To the contrary, in the tea group and the group of the product produced by fermenting with *Lactobacillus plantarum*, the total area of the erosions was 22.38±5.59% and 20.32±8.05%, respectively, and no significant difference from the control group was observed. On the other hand, in the group of the tea-added product produced by fermenting with *Lactobacillus plantarum*, the total area of the erosions was 4.46±2.12% and exhibited a remarkable suppression effect in comparison with the control group (p<0.05).

(3) Results

In the indomethacin-induced gastric ulcer model, the suppression effect of the formation of gastric ulcer due to the tea-added product produced by fermenting with *Lactobacillus plantarum* was confirmed. Further, in the hydrogen peroxide-induced gastric mucosal lesions, the effect of the administration of *Lactobacillus plantarum* cells or tea alone was not observed. The suppression effect was observed when they are used in combination.

It has hitherto been explained that the formation of gastric ulcer due to indomethacin is caused by deterioration of mucosal resistance and deterioration of blood flow due to the formation inhibition of prostaglandin. According to the latest report, it is confirmed to be connected with active oxygen due to arachidonic acid metabolic process and infiltration of neutrophil. It is considered that it is connected with active oxygen produced in the gastric mucosal ventriculi because the subcutaneous administration of indomethacin used at this time acts on the gastric mucosal through blood from the portion administered.

The formation of gastric ulcer was suppressed by the tea-added *Lactobacillus plantarum* and, at the same time, the SOD-like activity of the deproteinized component in the serum was increased. Therefore, it is considered that the antioxidation substance in the tea was absorbed to eliminate active oxygen in the gastric mucosal. It is also considered that examples of the gastric mucosal lesions due to the oral administration of hydrogen peroxide include direct mucosal disorder due to hydrogen peroxide and indirect disorder through infiltration of neutrophil. In both cases, hydrogen peroxide which is present in the gastric lumen acts as a induced substance. The fact that the gastric mucosal lesions induced by hydrogen peroxide was suppressed by administrating the tea and *Lactobacillus plantarum* cells in combination means that the Mn-CAT activity of *Lactobacillus planterum* cells acted effectively in the gastric lumen. On the other hand, the fact that the effective suppression effect was not exhibited by administrating *Lactobacillus plantarum* cells alone means that the CAT activity of the cells did not act in the gastric lumen, which reflects the results of Test Example 2.

Test Example 5

(MPO (myeloperoxidase) activity inhibition action of tea extract and catechin)

It has been know that the neutrophil produces active oxygen so as to detoxify foreign materials and bacteria in the living body. Particularly, the neutrophil has a dimutated system of hydrogen peroxide which is referred to as "MPO", thereby producing perchloric acid or monochloramine having high cytotoxicity. At the time of the excessive reaction, the transudation of the neutrophil to the exterior of MPO is confirmed and it is considered to be one factor to cause the disorder of the biomembrane. There is also a report that the infiltration of neutrophil is connected with its crisis mechanism in indomethacin-induced gastric ulcer and hydrogen peroxide-induced gastric mucosal lesions.

The meaning of the addition of the tea used as the manganese-containing natural material in the present invention is as described above. Further, it was examined in vitro whether the tea component inhibits the MPO activity or not.

To 2.9 ml of a 50 mM phosphate buffer (pH: 5.4) containing 0.1% hydrogen peroxide and 1.03 mM o-dianisidine, 50 µl of a test solution and 50 µl of a MPO purified enzyme (1.24 units/ml) were added and, after incubating in a cuvet at 25° C., measuring a change in absorbance (λ: 450 nm) was measured for 5 minutes. As a blank, 50 µl of a 50 mM phosphate buffer (pH: 5.4) was used.

As the test solution, a tea extract solution obtained by extracting a green tea with hot water and a solution obtained by measuring the concentration of Mn in the tea extract solution and adding $MnCl_2$ in an APT broth so that the concentration of Mn in the medium may be the same as that of the tea extract solution were used. Then, the MPO activity inhibition rate in each concentration of Mn. The results are shown in FIG. 9.

As is apparent from FIG. 9, the tea extract solution inhibits the MPO enzyme activity and the inhibition activity becomes higher as the concentration of Mn becomes higher. Further, it exhibits high inhibition rate in comparison with a Mn solution having the same concentration. It is considered to be connected with the tea component other than Mn.

Figure 10:
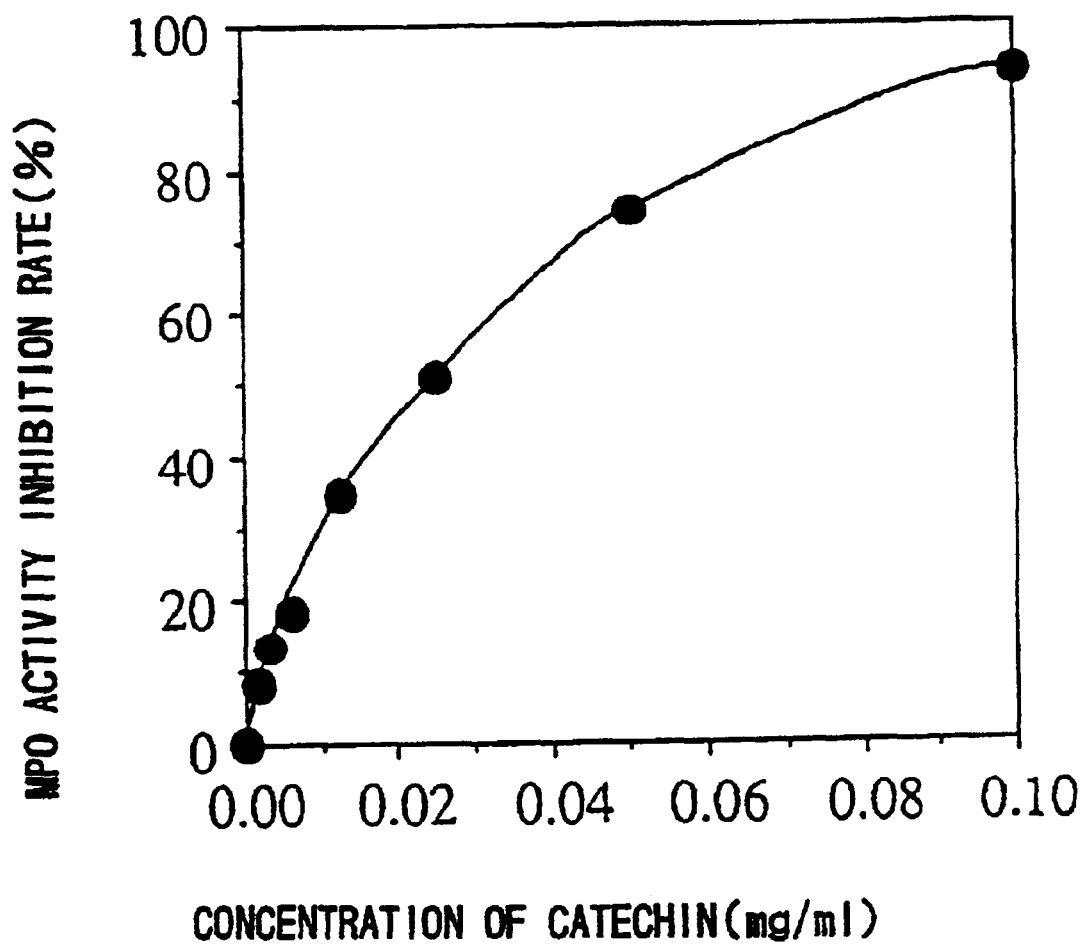
FIG. 10 is a graph illustrating a MPO activity inhibition effect of catechin.

Therefore, it was examined whether the component contained in the tea other than Mn is connected with the MPO activity inhibition or not. That is, according to the same manner as that described above, the MPO inhibition activity was examined using a purified catechin as the component other than Mn. The results are shown in FIG. 10. As is apparent from FIG. 10, catechin exhibits the inhibition effect in the concentration of 1.5 µg/ml or more.

As described above, the inhibition of the MPO activity due to the tea component was confirmed and, at the same time, it became apparent that Mn and catechin are connected with its activity inhibition.

Example 1 (Yogurt Type)

To 1 liter of sterilized milk, 4 g of a tea (powdered green tea) was added. *Lactobacillus plantarum* was inoculated into this milk wherein the tea had been added. Then, the fermentation was conducted for 18 hours while maintaining the temperature at 35 to 37° C.

The following yogurt forms could be prepared by adjusting the manufacturing conditions such as amount of the tea added, fermentation time, etc. according to a normal method.

a. Solid (set yogurt)
b. (Semi)solid (stirred yogurt)
c. Liquid (drink yogurt)

Example 2 (Lactic Acid Bacteria Beverage Type)

A tea (powdered green tea) was added to a predetermined amount of a mixed solution of skim milk and sucrose, and then *Lactobacillus plantarum* was inoculated into the mixed solution, which was fermented for 18 hours while maintaining the temperature at 37° C. Thereafter, the fermented solution was diluted with water and a stabilizer and a flavor were added to give a liquid yogurt type lactic acid bacteria beverage. The composition thereof is shown in Table 1.

Example 3 (Lactic Acid Bacteria Beverage Type)

A single cell tea (manufactured by Single Cell Foods Co., Ltd.) as the tea (powdered green tea) was added to a predetermined amount of a mixed solution of skim milk and sucrose, and then *Lactobacillus plantarum* was inoculated into the mixed solution, which was fermented for 18 hours while maintaining the temperature at 37° C. Thereafter, the fermented solution was diluted with water and orange juice, and a stabilizer and a flavor were added to give a juice type lactic acid bacteria beverage. The composition thereof is shown in Table 1.

TABLE 1

|  | Example 2<br>Drink yogurt type<br>% by weight | Example 3<br>Juice type<br>% by weight |
| --- | --- | --- |
| Raw material | | |
| Skim milk | 40.0 | 5.0 |
| Sucrose | 14.0 | 14.0 |
| Water | 45.0 | 70.0 |
| Tea | 0.4 | 0.4 |
| Fruit juice | 0.0 | 10.0 |
| Others[1)] | 0.6 | 0.6 |

[1)]Stabilizer, flavor, etc.

Example 4 (Freeze-Dried Type)

About $5\times10^{10}$ bacteria cells (*Lactobacillus plantarum*), 4 g of a tea (powdered green tea) and an excipient such as lactose and glucose were mixed and the mixture was freeze-dried to give a tablet type freeze-dried product. This product was suitable for ingesting as it is.

Example 5 (Freeze-Dried Type)

About $5\times10^{8}$ bacteria cells (*Lactobacillus plantarum*), 4 g of a tea (powdered green tea) and an excipient such as lactose and glucose were mixed and the mixture was freeze-dried to give a tablet type freeze-dried product. This product was added to commercially available milk and the mixture was fermented at room temperature for 12 to 24 hours. As a result, yogurt could be prepared. Accordingly, this freeze-dried product is suitable for preparing yogurt in the ordinary home.

What is claimed is:

1. A method for producing in vivo antioxidation in a living subject which comprises at least the following steps:
   (A) producing fermented milk by a process consisting essentially of the steps of:
      (1) preparing a mixed solution of milk and sugar with *Lactobacillus plantarum* ATCC 14431 cells having Mn-catalase activity,
      (2) fermenting the milk/sugar/bacteria cell solution with a powdered tea obtained from a manganese-containing tea,
         wherein the powdered tea is provided in an amount such that about $5\times10^{8}$ to $5\times10^{10}$ bacteria cells are present for 2 to 4 g of the powdered tea based on 1 liter of milk,
         wherein the fermenting is at 35–37° C. for 12–72 hours to provide a fermented milk product; and optionally,
      (3) adding a sweetener, a fruit flesh, an inorganic electrolyte, a vitamin and/or a flavor to the fermented milk product;
   (B) feeding the fermented milk of step (A) to the living subject,
   (C) producing superoxide dismutase activity and catalase activity in the living subject, and
   (D) removing superoxide and hydrogen peroxide in said living subject so as to effect in vivo antioxidation in said living subject.

2. A method for producing in vivo antioxidation in a living subject which comprises at least the following steps:
   (A) producing fermented milk by a process comprising the steps of:
      (1) preparing a mixed solution of milk and sugar with *Lactobacillus plantarum* ATCC 14431 cells having Mn-catalase activity,
      (2) fermenting the milk/sugar/bacteria cell solution with a powdered tea obtained from a manganese-containing tea,
         wherein the powdered tea is provided in an amount such that about $5\times10^{8}$ to $5\times10^{10}$ bacteria cells are present for 2 to 4 g of the powdered tea based on 1 liter of milk,
         wherein the fermenting is at 35–37° C. for 12–72 hours to provide a fermented milk product;
   (B) feeding the fermented milk of step (A) to the living subject,
   (C) expressing superoxide dismutase activity and catalase activity in the living subject, and
   (D) removing superoxide and hydrogen peroxide in said living subject so as to effect in vivo antioxidation in said living subject.

3. A method for producing in vivo antioxidation in a living subject which comprises at least the following steps:
   (A) producing a beverage by a process consisting essentially of the steps of:
      (1) preparing a mixed solution of milk and sugar with *Lactobacillus plantarum* ATCC 14431 cells having Mn-catalase activity,
      (2) fermenting the milk/sugar/bacteria cell solution with a powdered tea obtained from a manganese-containing tea,
         wherein the powdered tea is provided in an amount such that about $5\times10^{8}$ to $5\times10^{10}$ bacteria cells are present for 2 to 4 g of the powdered tea based on 1 liter of milk,
         wherein the fermenting is at 37° C. for 18 hours to provide a fermented milk product solution;
      (3) diluting the fermented solution with water and/or orange juice, and adding a stabilizer; and fermenting the milk/sugar/bacteria cell,
      (4) adding a flavor to the diluted fermented solution to give a liquid yogurt lactic acid bacteria beverage;
   (B) feeding the beverage of step (A) to the living subject,
   (C) expressing superoxide dismutase activity and catalase activity in the living subject, and
   (D) removing superoxide and hydrogen peroxide in said living subject so as to effect in vivo antioxidation in said living subject.

* * * * *